US009409929B2

(12) United States Patent
Shimada

(10) Patent No.: US 9,409,929 B2
(45) Date of Patent: Aug. 9, 2016

(54) (METH)ALLYLSILANE COMPOUND, SILANE COUPLING AGENT THEREFOR, AND FUNCTIONAL MATERIAL USING SAME

(75) Inventor: Toyoshi Shimada, Souraku-gun (JP)

(73) Assignees: KYOEISHA CHEMICAL CO., LTD., Osaka (JP); DAICEL CORPORATION, Osaka (JP); Toyoshi Shimada, Kyoto (JP)

( * ) Notice: Subject to any disclaimer, the term of this patent is extended or adjusted under 35 U.S.C. 154(b) by 0 days.

(21) Appl. No.: 14/129,416

(22) PCT Filed: Jun. 28, 2012

(86) PCT No.: PCT/JP2012/066599
§ 371 (c)(1),
(2), (4) Date: Jan. 31, 2014

(87) PCT Pub. No.: WO2013/002346
PCT Pub. Date: Jan. 3, 2013

(65) Prior Publication Data
US 2014/0142292 A1 May 22, 2014

(30) Foreign Application Priority Data
Jun. 29, 2011 (JP) ................. 2011-144725

(51) Int. Cl.
| | | |
|---|---|---|
| C07H 23/00 | (2006.01) | |
| C07F 7/08 | (2006.01) | |
| C08B 15/05 | (2006.01) | |
| C08B 37/16 | (2006.01) | |
| C09K 3/18 | (2006.01) | |
| C08K 9/06 | (2006.01) | |
| C08J 3/12 | (2006.01) | |
| C08K 9/08 | (2006.01) | |
| C03C 17/30 | (2006.01) | |
| C09C 3/12 | (2006.01) | |

(52) U.S. Cl.
CPC ............. *C07F 7/0818* (2013.01); *C03C 17/30* (2013.01); *C07F 7/081* (2013.01); *C07F 7/0812* (2013.01); *C07H 23/00* (2013.01); *C08B 15/05* (2013.01); *C08B 37/0012* (2013.01); *C08J 3/126* (2013.01); *C08J 3/128* (2013.01); *C08K 9/06* (2013.01); *C08K 9/08* (2013.01); *C09K 3/18* (2013.01); *C03C 2217/75* (2013.01); *C09C 3/12* (2013.01)

(58) Field of Classification Search
None
See application file for complete search history.

(56) References Cited

U.S. PATENT DOCUMENTS

| 5,667,674 A | 9/1997 | Hanggi et al. |
| 5,876,595 A | 3/1999 | Hanggi et al. |
| 5,968,652 A | 10/1999 | Hanggi et al. |
| 2004/0067436 A1 | 4/2004 | Kinsho et al. |
| 2008/0227939 A1 | 9/2008 | Mizoshita et al. |
| 2008/0227941 A1 | 9/2008 | Mizoshita et al. |
| 2009/0270590 A1* | 10/2009 | Jun et al. ................. 530/345 |
| 2013/0060014 A1 | 3/2013 | Jun et al. |

FOREIGN PATENT DOCUMENTS

| JP | A-2000-502952 | 3/2000 |
| JP | A-2004-175793 | 6/2004 |
| JP | A-2004-2384187 | 8/2004 |
| JP | A-2006-89588 | 4/2006 |
| JP | A-2008-214314 | 9/2008 |
| JP | A-2008-247886 | 10/2008 |
| JP | A-2009-502713 | 1/2009 |
| JP | A-2009-138097 | 6/2009 |
| JP | A-2010-90302 | 4/2010 |
| WO | 2007/024055 A1 | 3/2007 |
| WO | WO 2010/057080 A1 | 5/2010 |

OTHER PUBLICATIONS

Yamasaki, The 14th International Conference on Solid-State Sensors, Actuators and Microsystems, Ly, Franc, Jun. 10-14, 2007.*
Maegawa et al., "Preparation of Functionalized Aryl(diallyl)ethoxysilanes and their Palladium-Catalyzed Coupling Reactions Giving Sol-Gel Precursors," *Science Direct*, 2007, vol. 63, pp. 11467-11474.
Abel et al., "The Reaction of Perhalogenoketones with Allylic Derivatives of Silicon and Tin," *Journal of Organometallic Chemistry*, 1975, vol. 84, pp. 199-229.
International Search Report issued in International Patent Application No. PCT/JP2012/066599 dated Jul. 24, 2012.
Database CA [Online] Chemical Abstracts Service, XP-002734051, (1997), Klos et al., Aβ-Hydroxyethyl Carbanion Equivalent.
Boysen, et al., "Synthesis of Selectively Functionalized Carbosilane Dendrimers with a Carbohydrate Core," Organic Letters, vol. 1, No. 12, (1999), p. 1925-1927.

(Continued)

*Primary Examiner* — Layla Berry
(74) *Attorney, Agent, or Firm* — Oliff PLC

(57) ABSTRACT

A (meth)allylsilane compound chemically bonded to various alcohol derivatives including polyol derivatives such as saccharides, is raw material used to cause a substrate to express functionalities such as a defogging property and separation characteristics for column chromatography, can be easily prepared, is easily purified, and is stable and easy to handle, and a functional material in which those functionalities are expressed, while silyl group-containing groups are conveniently carried at a high density on the surface of the substrate, by using the (meth)allylsilane compound as a silane coupling agent for silane-coupling to the substrate. The (meth)allylsilane compound includes a (meth)allylsilyl group-containing alkyl group or a (meth)allylsilylalkyl group-containing aralkyl group that is bonded to an alcohol derivative. In the functional material, the silane coupling agent is ether-bonded to surface hydroxyl groups exposed on a substrate through the surface hydroxyl groups by silane coupling to have an ether bond on the functional material.

4 Claims, No Drawings

(56) References Cited

OTHER PUBLICATIONS

Chang, et al., "Amphiphilic Linear PEO—Dendritic Carbosilane Block Copolymers," Macromolecules (2000), 33, p. 4496-4500.
de Raadt, et al., "A one-step C-linked disaccharide synthesis from carbohydrate allylsilanes and tri-O-acetyl-D glucal," Carbohydrate Research, 220 (1991), p. 101-115.
Landais, et al., "A New Synthesis and Stereocontrolled Functionalization of Substituted Silacyclopent-3-enes," J. Org. Chem., (2003), 68, p. 2779-2789.
Jan. 19, 2015 extended European Search Report issued in European Application No. 12804224.9.
Apr. 9, 2015 Office Action issued in U.S. Appl. No. 14/129,824.
Klos et al.; "A b-Hydroxyethyl Carbanion Equivalent" J. Org. Chem. 1997; pp. 3758-3761; vol. 62.

* cited by examiner

(METH)ALLYLSILANE COMPOUND, SILANE COUPLING AGENT THEREFOR, AND FUNCTIONAL MATERIAL USING SAME

TECHNICAL FIELD

The present invention relates to a (meth)allylsilane compound that is used for a silane coupling reaction with a substrate to cause the substrate to express functionalities such as a defogging property and separation characteristics for column chromatography and is derived from an alcohol derivative, a silane coupling agent therefor, and a functional material using the same.

BACKGROUND ART

Organic/inorganic hybrid substances such as organic siloxane compounds have organic characteristics such as hydrophobicity attributable to organic groups and inorganic characteristics such as hydrophilicity and high reactivity with water or condensation reactivity attributable to siloxy groups. By polymerizing such organic/inorganic hybrid substances, specifically organic siloxanes containing a trialkoxysilyl group under a sol-gel reaction condition, a functional material having various functions such as refractive index-adjusting function, light absorption function, light emitting function or charge-transporting function is prepared.

However, the organic/inorganic hybrid substances preferentially and easily cause an exchange reaction of the trialkoxysilyl group with the alkoxy group and silanol group of other molecules as compared to polymerization reactions by the condensation, additive polymerization or the like of siloxy group-free chemical products or reagents, and thus do not cause a desired silane coupling reaction with the other functional groups. The organic/inorganic hybrid substances easily cause a hydrolysis reaction of the trialkoxysilyl group and thus are hard to cause a sol-gel reaction. And the organic/inorganic hybrid substances are unstable to water and moisture and thus are hard to be purified by silica gel column chromatography and also hard to be stored for a long time. Therefore, a functional material using a conventional organic/inorganic hybrid substance is poor in production efficiency, yield rate and purity.

Therefore, as shown in Non-Patent Document 1, the present inventors already disclosed the preparation of functional aryl(diallyl)ethoxysilanes that are used as precursors for sol-gel reactions, and palladium catalyst-coupling reactions thereof. Furthermore, as shown in Patent Document 1, the present inventors disclosed a process for obtaining an organic silica composite material such as a mesoporous body by subjecting an organic silane compound having an allyl group to hydrolysis and polycondensation reactions in a solvent.

An organic silane compound that has a higher reactivity than those of conventional organic/inorganic hybrid substances, has suitable hydrophilicity and hydrophobicity and steric characteristic and further has suitable reactivity and polycondensation property, and thus can be a silane coupling agent for expressing functionalities in substrates formed of various materials, has been desired.

PRIOR ART DOCUMENTS

Non-Patent Document

Non-Patent Document 1: Yoshifumi Maegawa et al., Tetrahedron, 2007, Vol. 63, p. 11467-11474

Patent Document

Patent Document 1: JP 2006-89588 A

SUMMARY OF INVENTION

Problem to be Solved by the Invention

The present invention was conducted for solving the above-mentioned problem, and aims at providing a (meth)allylsilane compound that is chemically bonded to various alcohol derivatives including polyol derivatives such as saccharides, is a raw material that is used to cause a substrate to express functionalities such as a defogging property and separation characteristics for column chromatography, can be conveniently prepared, is easily purified, and is stable and easy to handle; and a functional material in which functionalities such as a defogging property and separation characteristics for column chromatography are expressed, while silyl group-containing groups are conveniently carried at a high density on the surface of the substrate, by using the (meth) allylsilane compound as a silane coupling agent for silane-coupling to the substrate therewith.

Means for Solving Problem

The present invention is made for achieving the aforementioned object. A (meth)allylsilane compound comprises a (meth)allylsilyl group-containing alkyl group or a (meth) allylsilylalkyl group-containing aralkyl group, which optionally has substituents and is bonded to an alcohol derivative.

In the (meth)allylsilane compound, the alcohol derivative is a monool derivative, which is a saturated and/or unsaturated and linear, branched and/or cyclic derivative and selected from an alkyl alcohol and an aralkyl alcohol; or a polyol derivative, which is a saturated and/or unsaturated and linear, branched and/or cyclic derivative, and has polyhydric free hydroxyl groups or at least one free hydroxyl group with partially-protected polyhydric hydroxyl groups in polyhydric hydroxyl groups.

In the (meth)allylsilane compound, the alcohol derivative is the polyol derivative selected from saccharides and glycols.

In the (meth)allylsilane compound, the saccharides are any of monosaccharides, or polysaccharides selected from oligosaccharides, starches, celluloses, glycogens and cyclodextrins.

In the (meth)allylsilane compound, the monosaccharides are any of glucose derivatives, mannose derivatives, xylose derivatives and galactose derivatives, the oligosaccharides are any of sucrose derivatives and maltose derivatives, the starches are derivatives of amylose and/or amylopectin, the celluloses are any of cellulose, regenerated cellulose, cellulose ether derivatives and cellulose ester derivatives, the glycogens is glycogen, and the cyclodextrins are any of α-cyclodextrin derivatives, β-cyclodextrin derivatives and γ-cyclodextrin derivatives.

A silane coupling agent comprises the (meth)allylsilane compound.

A functional material is characterized in that the silane coupling agent is ether-bonded to surface hydroxyl groups exposed on a substrate through the surface hydroxyl groups by silane coupling to have an ether bond on the functional material.

In the functional material, at least one of the free hydroxyl groups derived from the alcohol derivative in the (meth)allylsilane compound is exposed.

In the functional material, the substrate is a glass substrate, a metal substrate, a ceramic substrate or a resin substrate. And the functional material is a defogging material that expresses a defogging property by the silane coupling agent.

In the functional material, the substrate is glass particles, silica gel particles, alumina particles, metal particles, ceramic particles, resin particles, or surface chemically-modified particles of any of those particles. And the functional material may be a column chromatography support that elutes and/or separates a solute by the hydrophilicity, hydrophobicity, adsorptive property and/or steric specificity of the silane coupling agent.

In the functional material, the ether bond is formed by the silane coupling reaction of the silane coupling agent by a sol-gel process.

In the functional material, the ether bond is formed by the silane coupling reaction of the silane coupling agent by a sol-gel process in an anhydrous organic solvent.

In the functional material, the ether bond is formed by the silane coupling of the silane coupling agent in the presence of at least any of hydrochloric acid, sulfuric acid, a tetraalkoxysilane, a polycarboxylic acid halide and a polycarboxylic acid anhydride.

A method for producing a functional material comprises: a step of conducting a silane coupling reaction, which the silane coupling agent reacts to a substrate having surface hydroxyl groups exposed thereon, to produce the functional material ether-bonded through the surface hydroxyl groups with the silane coupling agent.

In the method for producing a functional material, the ether bond is formed through the silane coupling reaction of the silane coupling agent by a sol-gel process.

The method for producing a functional material comprises: a step of treating the silane coupling agent with an acid aqueous solution; and subsequently the step of conducting the silane coupling reaction.

The method for producing a functional material comprises: the step of treating the silane coupling agent with the acid aqueous solution; and then steps of reacting tetraalkoxysilane therewith and reacting reactant in the presence of concentrated sulfuric acid; and subsequently the step of conducting the silane coupling reaction.

The method for producing a functional material comprises: a step of reacting the silane coupling agent with a polycarboxylic acid halide or a polycarboxylic acid anhydride, and subsequently the step of conducting the silane coupling reaction.

In the method for producing a functional material, the step of reacting with the polycarboxylic acid halide or the polycarboxylic acid anhydride is conducted in an anhydrous organic solvent.

Advantageous Effects of the Invention

The (meth)allylsilane compound of the present invention is bound to various alcohol derivatives, specifically polyol derivatives, more specifically stereospecific saccharides, which may have hydrophilic groups such as hydroxyl groups that easily provide hydrophilicity, by a chemical covalent bond, can be conveniently prepared in an efficient fashion with a high purity, is stable to water, moisture and solvents and thus is easily handled, does not decompose upon purification by silica gel chromatography or a distillation process under an ordinary to reduced pressure, and can be stored stably for a long term.

Since the (meth)allylsilane compound can induce suitable hydrophilicity and hydrophobicity and steric specificity, this is a raw material that is used for expressing functionalities such as a defogging property and separation characteristics for column chromatography in various substrates. Such (meth)allylsilane compound can allow various materials in planar forms such as a plate-like form, a film-like form and a sheet-like form, in three-dimensional structural forms such as a columnar form and a steric form and in particulate forms such as a powdery form or a granular form, specifically substrates formed from inorganic materials such as glass substrates, metal substrates and ceramic substrates or substrates formed from organic substrates such as a resin substrates to express functionalities such as a defogging property and separation characteristics for column chromatography.

Therefore, it is possible to conduct silane coupling with the functional groups of the substrate, specifically reactive functional groups such as hydroxyl groups that are originally present on the surface of the substrate or generated through a surface treatment, by using this (meth)allylsilane compound as an active ingredient for a silane coupling agent while utilizing an allyl group thereof.

When this silane coupling agent is used, it is possible to allow these substrates to express functionalities such as a defogging property and separation characteristics for column chromatography due to the (meth)allylsilane compound that exerts suitable hydrophilicity, hydrophobicity and steric specificity, and thus functional materials that are used in various fields can be conveniently produced. These functional materials can be used as defogging materials in housewares and electronic and electric apparatuses that should avoid fogging such as windows, eyeglasses and displays, and for precise and assured separation as supports for column chromatography for chemical analysis or isolation of test substances.

The method for producing a functional material can produce the functional material in which a desired function is surely and efficiently expressed in a conveniently manner with a fine yield and a high quality, over a wide scope from a laboratory scale to a plant scale.

MODE FOR CARRYING OUT THE INVENTION

Embodiments for carrying out the invention will be explained below in detail, but the scope of the present invention is not limited to these embodiments.

A (meth)allylsilane compound of the present invention includes a (meth)allylsilyl group-containing alkyl group or a (meth)allylsilylalkyl group-containing aralkyl group, which optionally has substituents and is bonded to a hydroxyl group of an alcohol derivative. This (meth)allyl may have substituents as long as it has an allyl carbon skeleton. Such (meth)allyl means an allyl group ($CH_2$=CH—$CH_2$—) or a methallyl group ($CH_2$=C($CH_3$)—$CH_2$—) optionally having substituents.

In the (meth)allylsilane compound, the alkyl group in this (meth)allylsilyl group-containing alkyl group includes linear, branched or cyclic and saturated or unsaturated alkyl groups with a carbon number of 1 to 18, preferably a carbon number of 3 to 6. Furthermore, the alkyl group in the (meth)allylsilylalkyl group-containing aralkyl group is the same as mentioned above, and the aralkyl group includes arylalkyl groups with a carbon number of 7 to 8 such as a benzyl group and a phenethyl group.

In the (meth)allylsilane compound, the (meth)allylsilyl group-containing alkyl group or the (meth)allylsilylalkyl group-containing aralkyl group may be directly bonded to the alcohol derivative. For example, the (meth)allylsilyl group-containing alkyl group or the (meth)allylsilylalkyl group-containing aralkyl group may be bonded by an ether bond to the alcoholic hydroxyl group of a monool derivative, or the alcoholic hydroxyl groups of a polyol derivative of a saccharide or a non-saccharide whose hydroxyl groups may be partially protected. Such ether bond is formed by, for example, Wilamson ether synthesis between a halide, or a tosylate or a mesylate of the (meth)allylsilyl group-containing alkyl group or (meth)allylsilylalkyl group-containing aralkyl group, and the alcoholic hydroxyl group of the alcohol derivative. Alternatively, the (meth)allylsilyl group-containing alkyl group or (meth)allylsilylalkyl group-containing aralkyl group may be bonded to any of the carbon atoms of the saccharide by a carbon-carbon covalent bond. Such carbon-carbon covalent bond may be formed by Grignard reaction between the aldehyde group, or hemiacetal group or hemiketal group of the saccharide and a Grignard reagent having the (meth)allylsilyl group-containing alkyl group or (meth)allylsilylalkyl group-containing aralkyl group.

The alcohol derivative may be a non-saccharide such as a monool derivative, which is a saturated and/or unsaturated and linear, branched and/or cyclic derivative, selected from alkyl alcohols having the same alkyl group as mentioned above and aralkyl alcohols having the same alkyl group as mentioned above. Also the alcohol derivative may be a polyol derivative such as a saccharide or glycol, which is a saturated and/or unsaturated and linear, branched and/or cyclic derivative that has polyhydric free hydroxyl groups or both of partially-protected polyhydric free hydroxyl groups and at least one free hydroxyl group.

Examples of a non-saccharide of the alcohol derivative include monool derivatives, which have one free hydroxyl group and may further have substituents, such as benzyl alcohol and phenethyl alcohol; and polyol derivatives, which have unprotected hydroxyl groups or plural free hydroxyl groups (i.e., polyhydric), or have partially-protected hydroxyl groups and at least one free hydroxyl group, and may further have substituents, such as glycols illustrated by ethylene glycol and glycerin.

A saccharide of the polyol derivative has unprotected hydroxyl groups or plural free hydroxyl groups (i.e., polyhydric), or has partially-protected hydroxyl groups and at least one free hydroxyl group, and may further have substituents. The polyol derivative having unprotected and unsubstituted hydroxyl groups may be a non-saccharide or saccharide that is exemplified by aliphatic alcohol derivatives having polyhydric hydroxyl groups, or aromatic derivatives having polyhydric hydroxyl groups, which are linear, branched and/or cyclic and saturated or unsaturated derivatives.

Examples of the saccharides include monosaccharides such as glucose derivatives, mannose derivatives, xylose derivatives and galactose derivatives; oligosaccharides that are disaccharides to pentasaccharides such as sucrose derivatives and maltose derivatives; starches that are polysaccharide derivatives containing amylose structures being linear forms and amylopectin structures being branched forms, both which are at a specific ratio due to a plant raw material; unsubstitited celluloses; regenerated celluloses such as rayon and cellophane; cellulose ether derivatives such as methyl cellulose and ethyl cellulose; cellulose ester derivatives such as nitrocellulose and acetylcellulose; glycogens such as glycogen; and cyclodextrins that are hexasaccharides to octasaccharides such as α-cyclodextrin derivatives, β-cyclodextrin derivatives and γ-cyclodextrin derivatives.

The polyol derivative may have unprotected and unsubstituted hydroxyl groups, or may have at least one free hydroxyl group and partially protected hydroxyl groups which is protected in a manner that allows deprotection or does not allow deprotection, and may optionally have further substituents.

Among these, it is further preferable that the polyol derivative is a saccharide optionally having substituents and optionally having protective groups.

The substituents that may be possessed by these include halogen atoms, alkyl groups or alkyloxy groups with a carbon number of 1 to 20, a nitro group, a cyano group, and aralkyl groups or aryl groups with a carbon number of 1 to 24. The substituents may be singular or plural.

Furthermore, examples of the protective groups for the saccharides include a benzyl group, an isopropylidene group, a methyl group, a p-methoxybenzyl group, a tert-butyl group, a methoxymethyl group, a 2-tetrahydropyranyl group, an acetyl group, a pivaloyl group, a benzoyl group, a trimethylsilyl group, a tert-butyldimethylsilyl group, a triisopropylsilyl group and a tert-butyldiphenylsilyl group.

The (meth)allylsilane compound is prepared, for example, in the following way. A tri(meth)allylsilyl group is formed by reacting a trihalogenosilyl group-containing compound such as one obtained by reacting a trihalogenosilane with the terminal of an olefin compound, with a Grignard reagent such as allylmagnesium bromide. Thereafter, where necessary, introduction of or conversion into a reactive functional group that may react to form a covalent bond of carbon-carbon or oxygen-carbon is conducted on an alcohol derivative to thereby prepare a precursor represented by the following chemical formula (I)

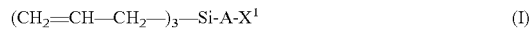

$$(CH_2=CH-CH_2-)_3-Si-A-X^1 \qquad (I)$$

(wherein in the chemical formula (I), -A- is a spacer group selected from an alkyl group and an alkylaralkyl group, $X^1$ is a leaving group such as a halogen atom or a p-toluenesulfonate ester group or a methanesulfonate ester group, or a reactive group such as a magnesium halide group that acts as a Grignard reagent).

When the free hydroxyl group of the alcohol derivative such as a polyol derivative and the precursor wherein $X^1$ in the chemical formula (I) is a leaving group are reacted, the dehydrogenated residue thereof binds to A by an ether bond through the free hydroxyl group, and then the protective group derived from the polyol derivative is deprotected as necessary, a (meth)allylsilane compound is obtained. Alternatively, when the aldehyde group, or the hemiacetal group or hemiketal group of the alcohol derivative such as a saccharide and the precursor wherein $X^1$ in the chemical formula (I) is a reactive group are reacted, a new carbon-carbon bond axis that is covalently bound to the aldehyde group or hemiacetal group is formed, and then the protective group derived from the polyol derivative is deprotected as necessary, a (meth)allylsilane compound is obtained.

A silane coupling agent of the present invention preferably contains the (meth)allylsilane compound as an active ingredient for silane coupling. The silane coupling agent may contain only this (meth)allylsilane compound as an active ingredient for silane coupling, and may further contain, in a concomitant manner, alkoxysilanes having an alkyl chain with a carbon number of 1 to 6 such as 1,2-bis(trialkoxysilyl) ethane; polycarboxylic acid halides such as oxalyl chloride, malonyl chloride, succinyl chloride and telephthaloyl chloride; and polycarboxylic acid anhydrides such as tartaric anhydride, phthalic anhydride and maleic anhydride as silane coupling components.

A functional material of the present invention includes an ether bond, which the silane coupling agent is ether-bonded to surface hydroxyl groups exposed on a substrate through at least partially hydroxyl groups of the surface hydroxyl groups by silane coupling.

In the functional material, the substrate may have a planar form such as a plate-like form, a film-like form and a sheet-like form, or a three-dimensional structural form such as a columnar form and a steric form. The substrate may be a glass substrate, a metal substrate, a ceramic substrate, or a resin substrate such as a thermoplastic resin, a thermosetting resin and a liquid crystal panel. And the functional material may be a defogging material that expresses a defogging property by having affinity for water such as water drops and moisture through the free hydroxyl groups of the alcohol derivative that constitutes the (meth)allylsilane compound in the silane coupling agent such as the polyol derivative.

In a functional material of another embodiment, a substrate thereof is powdery or granular particles having a weight average particle size or volume average particle size of 1 µm to 1 mm such as glass particles, silica gel particles, alumina particles, metal particles, ceramic particles, resin particles, or chemically-modified particles from any of these particles whose surfaces are coated with a metal, a metal oxide or a resin. Such functional material may be a column chromatography support that elutes and/or separates a solute such as a test substance to be analyzed by high-performance liquid chromatography and a crude composition to be purified by liquid chromatography, depending on the hydrophilicity that is attributed to the free hydroxyl groups as a hydrophilic group that are derived from the alcohol derivative such as the polyol derivative that constitutes the (meth)allylsilane compound in the silane coupling agent, the hydrophobicity that is attributed to the hydrophobic groups thereof, the adsorptive property that is attributed to the hydrophilic groups and hydrophobic groups thereof, and/or the steric specificity that is attributed to the steric configuration thereof.

The substrate may have natural surface hydroxyl groups that are originally exposed on the substrate itself, or may have fleshly-generated surface hydroxyl groups which are generated by an acid aqueous solution treatment for conducting a surface treatment through immersion or spraying of a strong acid such as diluted sulfuric acid or concentrated sulfuric acid, diluted hydrochloric acid or concentrated hydrochloric acid and diluted nitric acid or concentrated nitric acid, or a peroxide such as hydrogen peroxide, or may have fleshly-generated surface hydroxyl groups which are generated by a surface treatment with an alkali aqueous solution, a UV irradiation treatment, a corona discharge treatment or a plasma treatment.

The functional material is obtained in a manner, for example, such that propene is cleaved to give a di(meth)allylsilyl group by the silane coupling reaction of the surface hydroxyl group on the substrate with the tri(meth)allylsilyl group of the (meth)allylsilane compound in the silane coupling agent, and the di(meth)allylsilyl group is further converted to a mono(meth)allylsilyl group as necessary by reacting with the other surface hydroxyl group on the same substrate by silane coupling, and the mono(meth)allylsilyl group reacts with the other surface hydroxyl group of the same substrate by silane coupling as necessary, thereby a part or all of the tri(meth)allylsilyl groups are bound to the substrate by ether bonds through the surface hydroxyl groups of the substrate.

As mentioned above, the surface hydroxyl group of the substrate may be directly bonded to the silicon atom of the tri(meth)allylsilyl group or di(meth)allylsilyl group or mono (meth)allylsilyl group of/from the (meth)allylsilane compound in the silane coupling agent, by an ether bond through the oxygen atom of the surface hydroxyl group of the substrate.

Alternatively, the respective (meth)allylsilyl groups in the tri(meth)allylsilyl group, di(meth)allylsilyl group and mono (meth)allylsilyl group may be partially or entirely hydrolyzed under an acidic condition to thereby converted into silanol groups (SiOH groups). The silanol groups are condensed or polycondensed by reacting with the silicon atoms of the tri (meth)allylsilyl groups, di(meth)allylsilyl groups and mono (meth)allylsilyl groups of the co-existing other (meth)allyl-silane compound molecules or silanol groups that are similarly converted as mentioned above, or by reacting with the alkoxysilyl groups of the co-existing tetraalkoxysilane. However, the silanol groups, (meth)allylsilyl groups and alkoxysilyl groups are not completely condensed or polycondensed and at least some of them remain, depending on the reaction environments such as an acid strength, a temperature and a reaction time. Those are condensed with the surface hydroxyl groups of the substrate, for example, the surface hydroxyl groups, i.e., silanol groups of a glass substrate, glass particles or silica gel particles to thereby form new siloxane bonds (—Si—O—Si—), and the (meth)allylsilane compound in the silane coupling agent is finally carried on the substrate while undergoing functional group conversion.

When at least one of the free hydroxyl groups originated from the alcohol derivative such as a polyol derivative in the (meth)allylsilane compound is exposed, by subjecting the free hydroxyl groups to deprotection as necessary, on the functional material, the hydrophilicity is enhanced, and the functionalities such as a defogging property and separation characteristics for column chromatography are further improved.

Such functional material is produced as follows. By undergoing a step of conducting a silane coupling reaction by so-called a sol-gel process in which the silane coupling agent is applied onto the substrate having surface hydroxyl groups exposed thereon by painting, spraying, immersion or printing, and microparticles of the silane coupling agent are put into a solid state through a gel state from a sol state under which the microparticles are dispersed in a solution, the tri (meth)allylsilyl group and di(meth)allylsilyl group of the (meth)allylsilane compound in the silane coupling agent undergo a silane coupling reaction and bind by ether bonds through the surface hydroxyl groups, to thereby give a functional material.

The step of conducting a silane coupling reaction may also be executed after conducting a step of treating the silane coupling agent with an acid aqueous solution such as diluted hydrochloric acid, dilute sulfuric acid, diluted nitric acid and diluted acetic acid to thereby subject a part of, approximately all of or all of the tri(meth)allylsilyl group, di(meth)allylsilyl group or mono(meth)allylsilyl group of/from the (meth)allyl-silane compound in the silane coupling agent to silanol groups by functional group conversion. Alternatively, the step of conducting a silane coupling reaction may be executed after conducting a step of treating the silane coupling agent with an acid aqueous solution to thereby form silanol groups, a step of subjecting the silanol groups to a condensation or polycondensation reaction with a tetraalkoxysilane to conduct functional group conversion of the silanol groups to siloxy groups, and a step of subjecting the silanol groups, siloxy groups and alkoxysilyl groups to a polycondensation reaction with concentrated sulfuric acid to conduct functional group conversion to other siloxy groups. Alternatively the step of conducting a silane coupling reaction may be executed after conducting a step of subjecting the silane coupling agent to an esterification reaction with a polycarboxylic acid halide or a polycarboxylic acid anhydride to thereby convert the silane coupling agent to an oligomer. The step of treating with a polycarboxylic acid halide or a polycarboxylic acid anhydride is preferably conducted in an anhydrous organic solvent, specifically in a water-insoluble organic solvent such as methylene chloride and toluene. Where necessary, it is preferable that the protective groups derived from the alcohol derivative such as a polyol derivative are deprotected to cause the free hydroxyl group to expose.

The functional material obtained by this way is used as a defogging material for housewares and electronic and electric apparatuses that should avoid fogging by vapor or moisture, and as a support for high-pressure column chromatography, affinity column chromatography, or optically active column chromatography by which asymmetry can be identified.

DESCRIPTION OF EMBODIMENTS

Hereinafter Examples of a (meth)allylsilane compound, a silane coupling agent therefor, and a functional material using the same for which the present invention is applied, and Comparative Examples for which the present invention is not applied, will be explained along with actual examples.

Example 1

(1.1) Cyclopentyl methyl ether (CPME) (90 ml) was added to 1,4-dibromobenzene (1) (15 g, 15.9 mmol) under a nitrogen atmosphere, the mixture was cooled to around −10° C. with brine ice, a solution of 2 M isopropylmagnesium chloride in tetrahydrofuran (THF) ($^i$PrMgCl solution) (0.35 equivalent amount, 11.2 ml) and a solution of 1.67 M n-butyllithium in hexane ($^n$BuLi solution) (0.7 equivalent amount, 26.8 ml) were respectively added dropwise. The mixture was stirred at around −10° C. for 2 hours, allyl bromide (1.1 equivalent amount, 6.8 ml) was then added, and the mixture was stirred at room temperature for 14 hours. Diethyl ether was added to the reaction mixture, and the mixture was neutralized with a saturated aqueous solution of ammonium chloride. The aqueous layer was extracted with diethyl ether, and the combined organic layer was washed with saturated brine, dried over anhydrous magnesium sulfate, filtered, and concentrated under a reduced pressure to give a crude product of 1-allyl-4-bromobenzene (2) (yield amount: 13.0 g, tentative yield: 103%), as shown in the following chemical reaction formula.

[Chemical Formula 1]

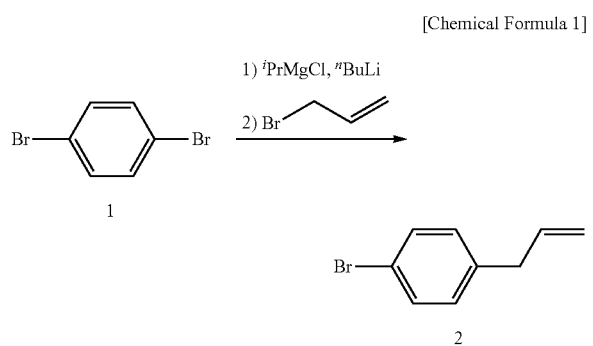

A physical and chemical analysis by a $^1$H-nuclear magnetic resonance spectrometry ($^1$H NMR) was conducted on this crude product, and the result thereof is shown below.

$^1$H NMR (CDCl$_3$) δ=7.41 (d, J=8.0 Hz, 2H), 7.06 (d, J=8.0 Hz, 2H), 5.88-5.96 (m, 1H), 5.05-5.09 (m, 2H), 3.33 (d, J=6.8 Hz, 2H)

The result of this physical and chemical analysis supports the chemical structure of the chemical formula (2).

(1.2) Distilled methylene chloride (25 ml) and distilled diethyl ether (25 ml) were added to 1-allyl-4-bromobenzene (2) (13.2 g, 55.1 mmol) and (Bu$_4$N)$_2$[PtCl$_6$] (50.0 mg, 0.1 mol %) under a nitrogen atmosphere, the mixture was cooled to 0° C., trichlorosilane (2 equivalent amount, 11.1 ml) was added thereto, and the mixture was stirred at room temperature for 12 hours. Thereafter the reactant was concentrated under a reduced pressure and cooled to 0° C. under a nitrogen atmosphere, thereafter a solution of 1 M allylmagnesium bromide in diethyl ether (CH$_2$=CH—CH$_2$—MgBr solution) (4 equivalent amount, 220.4 ml) was added dropwise thereto, and the mixture was stirred at room temperature for 15 hours. Diethyl ether was added to the reaction mixture, and the mixture was neutralized with a saturated aqueous solution of ammonium chloride. The aqueous layer was extracted with dimethyl ether, and the combined organic layer was washed with saturated brine, dried over anhydrous magnesium sulfate, filtered, and concentrated under a reduced pressure to give a crude product. The crude product was purified by separating by silica gel column chromatography (elution solvent: n-hexane) to give 4-{3-(triallylsilyl)propyl}phenylbromide (3) (yield amount: 16.3 g, yield: 87%), as shown in the following chemical reaction formula.

[Chemical Formula 2]

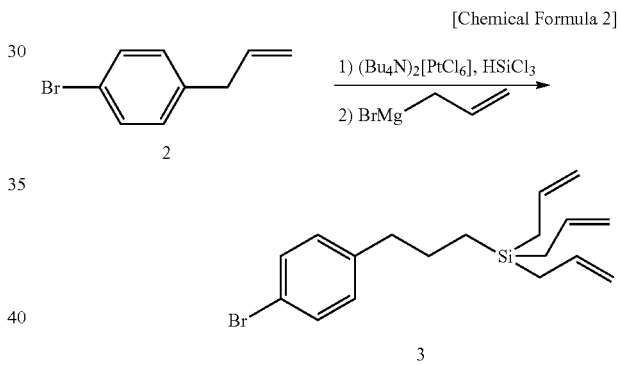

The result of the physical and chemical analysis of this by $^1$H NMR is shown below.

$^1$H NMR (CDCl$_3$) δ=7.81 (d, J=8.0 Hz, 2H), 7.32 (d, J=8.0 Hz, 2H), 5.70-5.82 (m, 3H), 4.84-4.89 (m, 6H), 2.70 (t, J=3.4 Hz, 2H), 1.62-1.66 (m, 2H), 1.58 (d, J=7.6 Hz, 6H), 0.58-0.63 (m, 2H)

The result of this physical and chemical analysis supports the chemical structure of the chemical formula (3).

(1.3) THF (50 ml) was added to 4-{3-(triallylsilyl)propyl}phenylbromide (3) (14.2 g, 40.6 mmol) under a nitrogen atmosphere, the mixture was cooled to around −10° C. with brine ice, and a solution of 2 M $^i$PrMgCl (0.70 equivalent amount, 14.2 ml) and a solution of 1.67 M $^n$BuLi (1.4 equivalent amount, 34.0 ml) were respectively added dropwise. The mixture was stirred at around −10° C. for 2 hours, N,N-dimethylformamide (DMF) (2 equivalent amount, 6.3 ml) was then added, and the mixture was stirred at room temperature for 14 hours. Diethyl ether was added to the reaction mixture, and the mixture was neutralized with a saturated aqueous solution of ammonium chloride. The aqueous layer was extracted with diethyl ether, and the combined organic layer was washed with saturated brine, dried over anhydrous magnesium sulfate, filtered, and concentrated under a reduced pressure to give a crude product. The crude product was purified by separating by silica gel column chromatography (elution solvent: hexane/ethyl acetate=20/1) to give 4-{3-(triallylsilyl)propyl}benzaldehyde (4) (yield amount: 11.0 g, yield: 89%), as shown in the following chemical reaction formula.

[Chemical Formula 3]

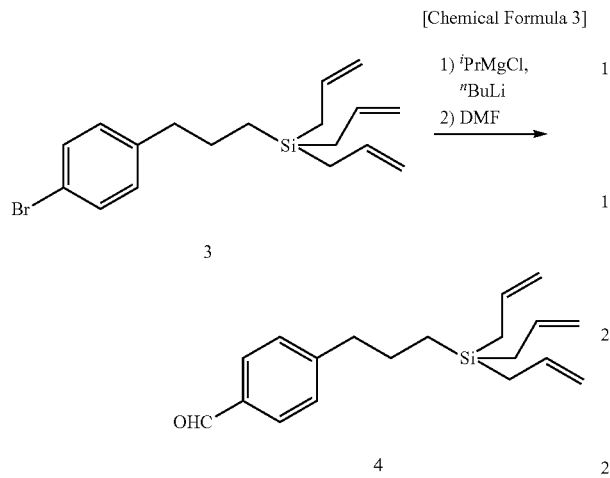

The result of the physical and chemical analysis of this by $^1$H NMR is shown below.

$^1$H NMR (CDCl$_3$) δ=9.98 (s, 1H), 7.78 (d, J 6.8 Hz, 2H), 7.32 (d, J=7.2 Hz, 2H), 5.70-5.81 (m, 3H), 4.84-4.89 (m, 6H), 2.68 (t, J=3.6 Hz, 2H), 1.66-1.70 (m, 2H), 1.58 (d, J=7.6 Hz, 6H), 0.61-0.65 (m, 2H)

The result of this physical and chemical analysis supports the chemical structure of the chemical formula (4).

(1.4) THF (25 ml) and methanol (MeOH) (25 ml) were added to 4-{3-(triallylsilyl)propyl}benzaldehyde (4) (11.0 g, 36.9 mmol) under a nitrogen atmosphere, the mixture was cooled to around 0° C. with ice, NaBH$_4$ (2.8 g, 73.8 mmol) was added thereto, and the mixture was stirred for 3 hours. An aqueous solution of saturated sodium hydrogen carbonate was added to the reaction mixture. The aqueous layer was extracted with diethyl ether, and the combined organic layer was washed with saturated brine, dried over anhydrous magnesium sulfate, filtered, and concentrated under a reduced pressure to give a crude product. The crude product was purified by separating by silica gel column chromatography (elution solvent: n-hexane/ethyl acetate=5/1) to give 4-{3-(triallylsilyl)propyl}benzyl alcohol (5) (yield amount: 9.2 g, yield: 84%), as shown in the following chemical reaction formula.

[Chemical Formula 4]

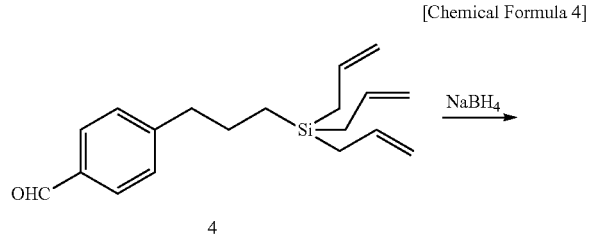

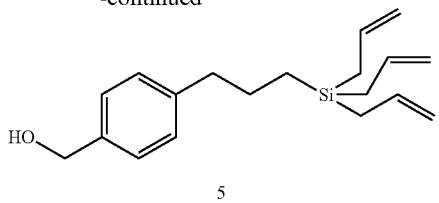

The result of the physical and chemical analysis of this by $^1$H NMR is shown below.

$^1$H NMR (CDCl$_3$) δ=7.29 (d, J=7.6 Hz, 2H), 7.16 (d, J=8.0 Hz, 2H), 5.72-5.80 (m, 3H), 4.84-4.89 (m, 6H), 4.67 (d, J=4.4 Hz, 2H), 2.61 (t, J=7.4 Hz, 2H), 1.60-1.68 (m, 2H), 1.58 (d, J=7.6 Hz, 6H), 0.62-0.66 (m, 2H)

The result of this physical and chemical analysis supports the chemical structure of the chemical formula (5).

(1.5) 5 ml of methylene chloride and CBr$_4$ (4.97 g, 15.0 mmol) were slowly added to 4-{3-(triallylsilyl)propyl}benzyl alcohol (5) (3.0 g, 10.0 mmol) and triphenylphosphine (PPh$_3$) (3.93 g, 15.0 mmol) under a nitrogen atmosphere, and the mixture was stirred for 1 hour. Cooled distilled water was added to the reaction mixture. The aqueous layer was extracted with methylene chloride, and the combined organic layer was dried over anhydrous sodium sulfate, filtered, and concentrated under a reduced pressure to give a crude product. The crude product was purified by separating by silica gel column chromatography (elution solvent: n-hexane/ethyl acetate=20/1) to give 4-{3-(triallylsilyl)propyl}benzyl bromide (6) (yield amount: 2.80 g, yield: 77%), as shown in the following chemical reaction formula.

[Chemical Formula 5]

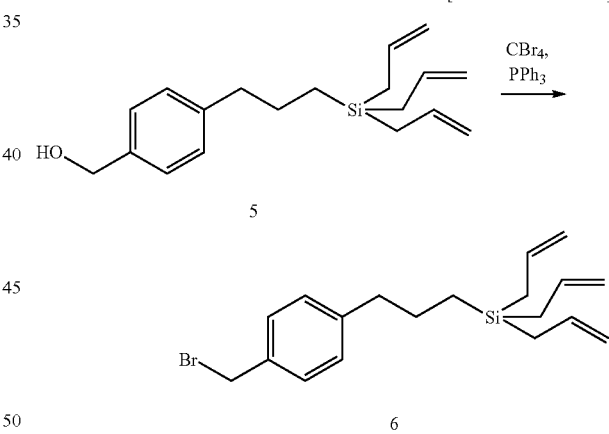

The result of the physical and chemical analysis of this by $^1$H NMR is shown below.

$^1$H NMR (CDCl$_3$) δ=7.31 (d, J=3.6 Hz, 2H), 7.13 (d, J=8.4 Hz, 2H), 5.75 (m, 3H), 4.86 (m, 6H) 4.45 (s, 2H), 2.61 (t, J=7.4 Hz, 2H) 1.61-1.67 (m, 2H), 1.57 (d, J=7.6 Hz, 6H), 0.61-0.65 (m, 2H)

The result of this physical and chemical analysis supports the chemical structure of the chemical formula (6).

(1.6) 5 ml of DMF was added to (±)-α-methyl-D-glucose (7) (500 mg, 2.58 mmol), benzaldehyde dimethylacetal (412 mg, 2.71 mmol) and p-toluenesulfonic acid monohydrate (491 mg, 2.58 mmol), and the mixture was subjected to a sonication treatment for 7 minutes. Triethylamine was added to the reaction mixture, and the mixture was filtered and concentrated under a reduced pressure to give a crude product. The crude product was purified by separating by silica gel column chromatography (elution solvent: chloroform/methanol=20/1) to give (+)-(4,6-O-benzylidene)methyl-α-D-glucopyranoside (8) (yield amount: 248 mg, yield: 34%), as shown in the following chemical reaction formula.

[Chemical Formula 6]

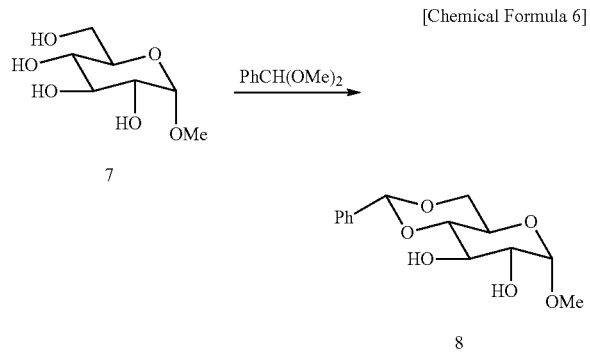

The result of the physical and chemical analysis of this by $^1$H NMR is shown below.

$^1$H NMR (CDCl$_3$) δ=7.48 (dd, J=3.6 Hz, J=3.0 Hz, 2H), 7.35-7.39 (m, 3H), 5.49 (s, 1H), 4.71 (d, J=4.0 Hz, 1H), 4.26 (dd, J=5.6 Hz, J=4.2 Hz, 1H), 3.89 (t, J=9.6 Hz, 1H), 3.69-3.80 (m, 2H), 3.56 (dd, J=5.2 Hz, J=3.8 Hz, 1H), 3.44 (t, J=9.4 Hz, 1H), 3.40 (s, 3H)

The result of this physical and chemical analysis supports the chemical structure of the chemical formula (8).

(1.7) NaH (10 equivalent amount, 72.3 mg, 1.77 mmol) was washed three times with n-hexane under a nitrogen atmosphere, tetrabutylammonium iodide (TBAI) (6.54 mg, 10 mol %) and (+)-(4,6-O-benzylidene)methyl-α-D-glucopyranoside (8) (1 equivalent amount, 50 mg, 0.177 mmol) dissolved in 5 ml of THF were added thereto, the mixture was stirred for 30 minutes, 4-{3-(triallylsilyl)propyl}benzyl bromide (6) (371.1 mg, 1.06 mol) was then added, and the mixture was stirred for 15 hours. Thereafter methanol was added thereto, and the mixture was stirred for 30 minutes and slowly poured into ice/diethyl ether. The reaction mixture was neutralized by adding 1N diluted hydrochloric acid, and an aqueous solution of saturated sodium hydrogen carbonate was added. The aqueous layer was extracted with diethyl ether, and the combined organic layer was washed with saturated brine, dried over anhydrous sodium sulfate, filtered, and concentrated under a reduced pressure to give a crude product. The crude product was purified by separating by silica gel column chromatography (elution solvent: n-hexane/ethyl acetate=gradually changed from 20/1 to 2/1) to give an allylsilane compound (9) (yield amount: 27 mg, yield: 41%) to which the present invention is applied, as shown in the following chemical reaction formula.

[Chemical Formula 7]

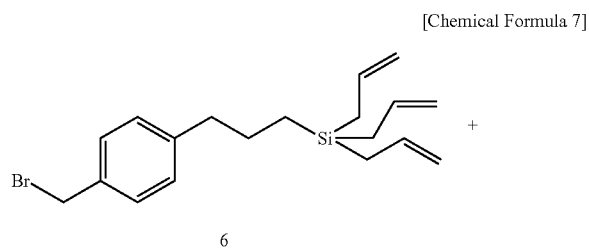

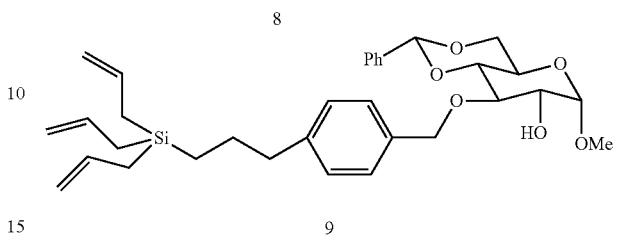

The result of the physical and chemical analysis of this by $^1$H NMR is shown below.

$^1$H NMR (CDCl$_3$) δ=7.48 (dd, J=4.8 Hz, J=2.0 Hz, 2H), 7.35-7.39 (m, 3H), 7.30 (d, J=7.6 Hz, 2H), 7.16 (d, J=7.6 Hz, 2H), 5.71-5.81 (m, 3H), 5.52 (s, 1H), 4.84-4.90 (m, 6H), 4.71 (q, J=16 Hz, J=12.2 Hz, 2H), 4.61 (d, J=3.6 Hz, 1H), 4.26 (dd, J=5.6 Hz, J=4.6 Hz, 1H), 4.14 (t, J=9.2 Hz, 1H), 3.78-3.84 (m, 1H), 3.70 (t, J=10.0 Hz, 2H), 3.44-3.52 (m, 1H), 3.38 (s, 1H), 2.61 (t, J=7.6 Hz, 2H), 1.62-1.74 (m, 2H), 1.57 (d, J 8.4 Hz, 6H), 0.61-0.65 (m, 2H)

The result of this physical and chemical analysis supports the chemical structure of the chemical formula (9).

(1.8) The allylsilane compound of the chemical formula (9) is used as a functional material, after being formed into a defogging material by attaching the compound to a glass, or after being formed into a column chromatography support by which asymmetry can be identified, by attaching the compound to a substrate for a chromatography support such as a silica gel and a resin powder.

Example 2

(2.1) NaH (1.2 equivalent amount, 157 mg, 3.92 mmol) was washed three times with hexane under a nitrogen atmosphere, tetrabutylammonium iodide (TBAI) (120 mg, 10 mol %) and 1,2:5,6-di-O-isopropylidene-α-D-glucofuranose (10) (1 equivalent amount, 850 mg, 3.27 mmol) dissolved in 20 ml of THF were added thereto, the mixture was stirred for 30 minutes, 4-{3-(triallylsilyl)propyl}benzyl bromide (6) (1.2 equivalent amount, 1.42 g, 3.92 mmol) was then added, and the mixture was stirred for 15 hours. Thereafter methanol was added thereto, and the mixture was stirred for 30 minutes and slowly poured to ice/diethyl ether. The reaction mixture was neutralized by adding 1N diluted hydrochloric acid, and an aqueous solution of saturated sodium hydrogen carbonate was added. The aqueous layer was extracted with diethyl ether, and the combined organic layer was washed with saturated brine, dried over anhydrous sodium sulfate, filtered, and concentrated under a reduced pressure to give a crude product. The crude product was purified by separating by silica gel column chromatography (elution solvent: n-hexane/ethyl acetate=5/1) to give an allylsilane compound (11) (yield amount: 1250 mg, yield: 71%) to which the present invention is applied, as shown in the following chemical reaction formula.

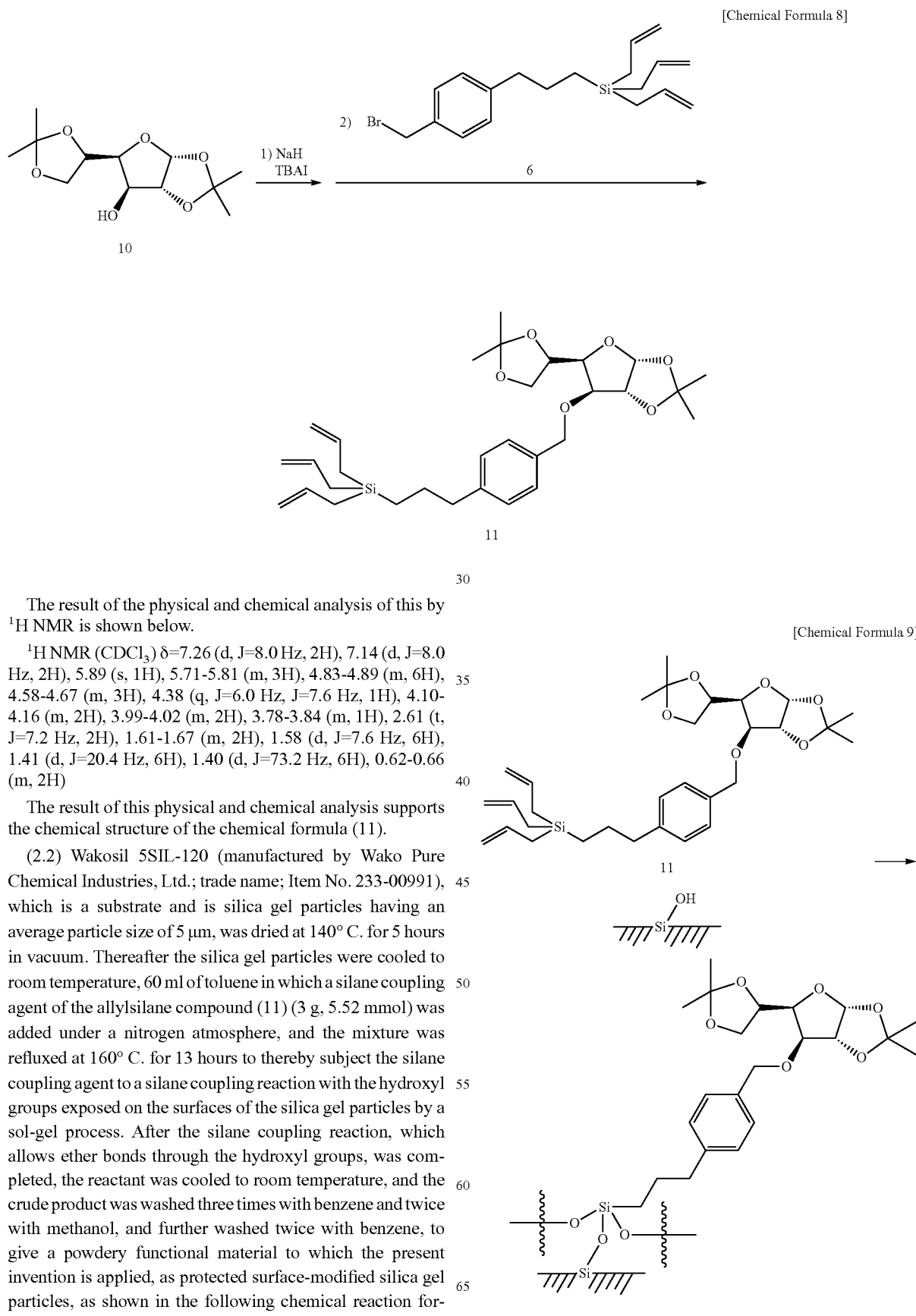

The result of the physical and chemical analysis of this by $^1$H NMR is shown below.

$^1$H NMR (CDCl$_3$) δ=7.26 (d, J=8.0 Hz, 2H), 7.14 (d, J=8.0 Hz, 2H), 5.89 (s, 1H), 5.71-5.81 (m, 3H), 4.83-4.89 (m, 6H), 4.58-4.67 (m, 3H), 4.38 (q, J=6.0 Hz, J=7.6 Hz, 1H), 4.10-4.16 (m, 2H), 3.99-4.02 (m, 2H), 3.78-3.84 (m, 1H), 2.61 (t, J=7.2 Hz, 2H), 1.61-1.67 (m, 2H), 1.58 (d, J=7.6 Hz, 6H), 1.41 (d, J=20.4 Hz, 6H), 1.40 (d, J=73.2 Hz, 6H), 0.62-0.66 (m, 2H)

The result of this physical and chemical analysis supports the chemical structure of the chemical formula (11).

(2.2) Wakosil 5SIL-120 (manufactured by Wako Pure Chemical Industries, Ltd.; trade name; Item No. 233-00991), which is a substrate and is silica gel particles having an average particle size of 5 μm, was dried at 140° C. for 5 hours in vacuum. Thereafter the silica gel particles were cooled to room temperature, 60 ml of toluene in which a silane coupling agent of the allylsilane compound (11) (3 g, 5.52 mmol) was added under a nitrogen atmosphere, and the mixture was refluxed at 160° C. for 13 hours to thereby subject the silane coupling agent to a silane coupling reaction with the hydroxyl groups exposed on the surfaces of the silica gel particles by a sol-gel process. After the silane coupling reaction, which allows ether bonds through the hydroxyl groups, was completed, the reactant was cooled to room temperature, and the crude product was washed three times with benzene and twice with methanol, and further washed twice with benzene, to give a powdery functional material to which the present invention is applied, as protected surface-modified silica gel particles, as shown in the following chemical reaction formula.

(2.3) Such allylsilane compound of the chemical formula (11) is used as a functional material, after being formed into a defogging material, by attaching the compound to a glass, or after being formed into a column chromatography support by which asymmetry can be identified, by attaching the compound to a substrate for a chromatography support such as a silica gel and a resin powder, and by being further deprotected or by introducing other functional groups thereinto as necessary. For example, the allylsilane compound was deprotected and reacted with dimethylphenylisocyanate (DMP) as follows to give a DMP-modified functional material.

(2.4) At first, the deprotection was conducted as follows. 1.5 g of the protected surface-modified silica gel particles obtained in the above-mentioned (2.2) was weighed, dispersed in a mixed solution of 7.0 ml of isopropanol (IPA), 3.0 ml of water and 0.13 ml of trifluoroacetic acid (TPA), and heated for 7 hours under stirring while keeping at 50 to 52° C. The product was allowed to cool and left overnight, and separated by filtration by a glass filter, washed four times with 25 ml of IPA, once with 20 ml of methanol, once with 20 ml of IPA and twice with 20 ml of hexane in this order, dried in the air, and farther dried under vacuum for 5 hours at 65° C. to give deprotected surface-modified silica gel particles, as shown in the following chemical reaction formula.

[Chemical Formula 10]

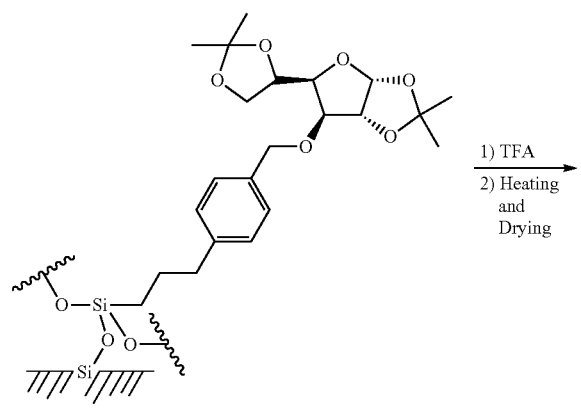

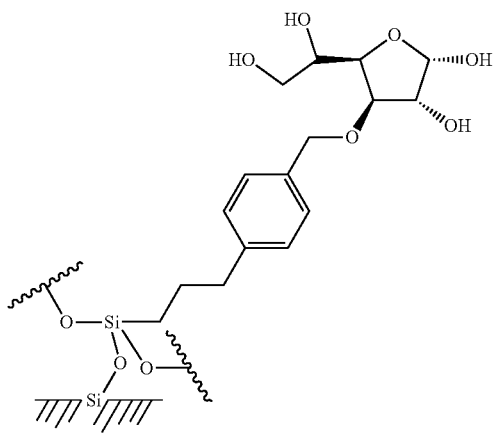

(2.5) Next, modification with DMP was conducted as follows. 52.7 mg of the deprotected surface-modified silica gel particles obtained in the above-mentioned (2.4) was weighed, 1.0 ml of pyridine and 150 µl of 3,5-dimethylphenylisocyanate were added under a nitrogen airflow, and the mixture was kept at 75° C. for 8 hours under stirring. The product was allowed to cool, 10 ml of IPA was added thereto, and the mixture was left overnight, the crystalline product was dissolved by a mixed solvent of 5 ml of methanol, 5 ml of acetone and 10 ml of N,N-dimethylformamide (DMF), the solution was transferred to a glass filter, and the inner wall of the vessel was thoroughly washed with 10 ml of DMF, to thereby separate a crude product of DMP-modified surface-modified silica gel particles by filtration. Furthermore, the product was washed three times with 20 ml of DMF, four times with 20 ml of ethanol and twice with 10 ml of hexane, dried in the air, and further dried in vacuum for 5 hours at 65° C., to thereby give DMP-modified surface-modified silica gel particles, as shown in the following chemical reaction formula.

[Chemical Formula 11]

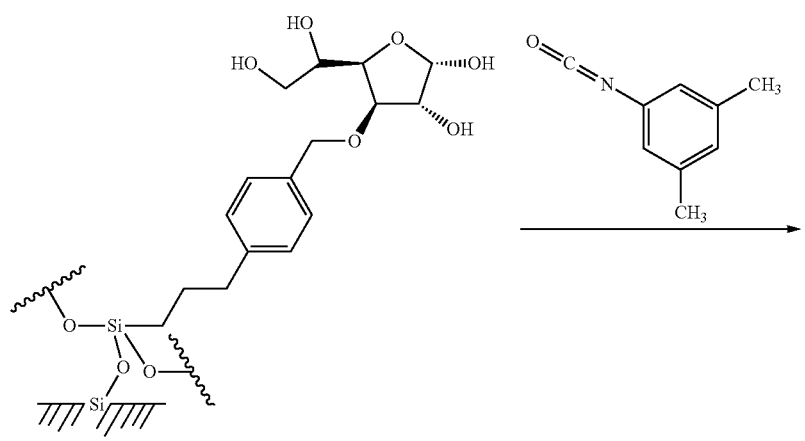

-continued

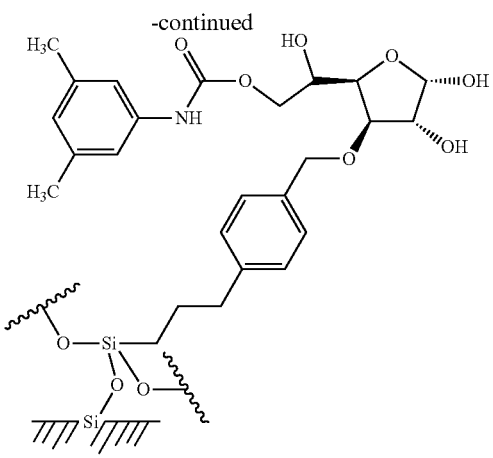

When the obtained DMP-modified surface-modified silica gel particles were subjected to an elementary analysis, the measured values were C, 12.15%; H, 1.69%; and N, 0.67%; and these were approximately the theoretical values. Furthermore, when the DMP-modified surface-modified silica gel particles were subjected to an infrared ray absorption spectroscopy, a C=O stretching vibration was observed at 1716 $cm^{-1}$, and an NH bending vibration was observed at 1618 $cm^{-1}$.

The result of this physical and chemical analysis supports the chemical structure of the DMP-modified surface-modified silica gel particles.

Example 3

(3.1) 3-Bromopropyltrichlorosilane (12) (1 equivalent amount, 5 g, 19.5 mmol) was cooled to 0° C. under a nitrogen atmosphere, a solution of 1 M allylmagnesium bromide (3.3 equivalent amount, 64.5 ml) was added thereto, and the mixture was stirred at room temperature for 3 hours. Diethyl ether was added to the reaction mixture, and the mixture was neutralized with an aqueous solution of citric acid. The aqueous layer was extracted with diethyl ether, and the combined organic layer was washed with saturated brine, dried over anhydrous magnesium sulfate, filtered, and concentrated under a reduced pressure to give a crude product. The crude product was purified by separation by silica gel column chromatography (elution solvent: n-hexane) to give 3-bromopropyltriallylsilane (13) (yield amount: 5.2 g, yield: 98%).

[Chemical Formula 12]

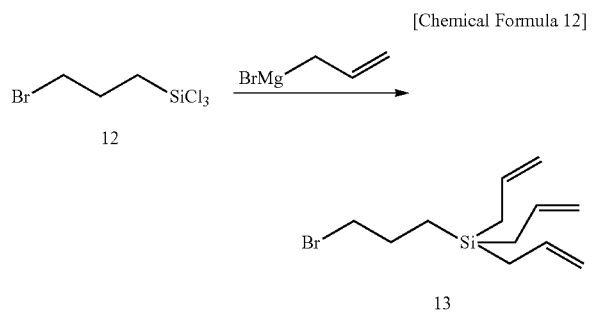

The result of the physical and chemical analysis of this by $^1$H NMR is shown below.

$^1$H NMR (CDCl$_3$) δ=5.73-5.81 (m, 3H), 4.88-4.93 (m, 6H), 3.37 (t, J=7.2 Hz, 2H), 1.86-1.90 (m, 2H), 1.61 (d, J=8.4 Hz, 6H), 0.69-0.74 (m, 2H)

The result of this physical and chemical analysis supports the chemical structure of the chemical formula (13).

(3.2) 5 ml of diethyl ether was added to magnesium particles (934 mg, 38.4 mmol) activated with iodine, 3-bromopropyltriallylsilane (13) (7.0 g, 25.2 mmol) dissolved in 20 ml of diethyl ether was added dropwise slowly, and the mixture was stirred at room temperature for 13 hours to give a diethyl ether solution of 3-(triallylsilyl)propylmagnesium bromide (14), as shown in the following chemical reaction formula.

[Chemical Formula 13]

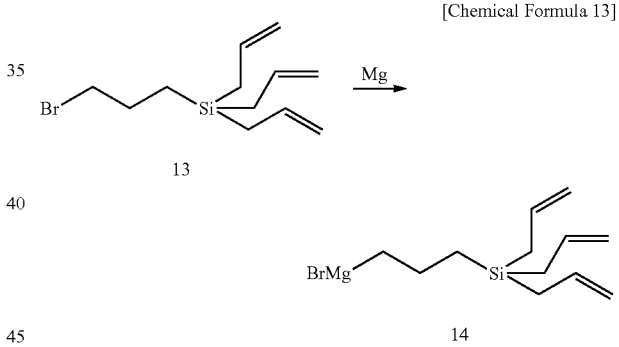

Thereafter the concentration of the solution was measured by acid-base titration and found to be 0.78 M. Subsequently, 20 ml of THF was added to 2,3:5,6-di-O-isopropylidene-α-D-mannofuranose (15) (1 g, 3.84 mmol), the mixture was cooled to 0° C., a diethyl ether solution of 3-(triallylsilyl)propylmagnesium bromide (14) (4.0 equivalent amount, 19.7 ml) was added thereto, and the mixture was stirred at room temperature for 5 hours. Diethyl ether was added to the reaction mixture, and the mixture was neutralized with an aqueous solution of citric acid. The aqueous layer was extracted with diethyl ether, and the combined organic layer was washed with saturated brine, dried over anhydrous magnesium sulfate, filtered, and concentrated under a reduced pressure to give a crude product. The crude product was dissolved in a mixed solvent of hexane and methanol, and only the methanol layer was combined by separation and concentrated under a reduced pressure to give an allylsilane compound (16) (yield amount: 5.2 g, yield: 68%) to which the present invention is applied, as shown in the following chemical reaction formula.

[Chemical Formula 14]

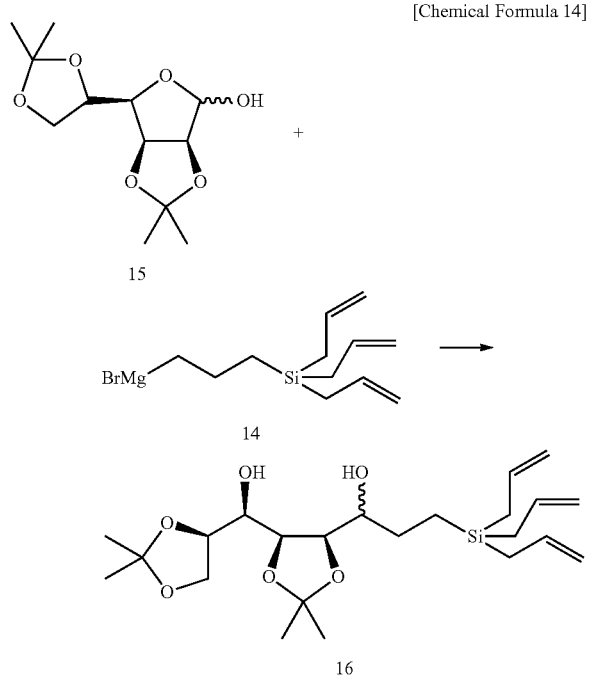

The result of the physical and chemical analysis of this by $^1$H NMR is shown below.

$^1$H NMR (CDCl$_3$) δ=5.73-5.82 (m, 3H), 4.84-4.91 (m, 6H), 4.30-4.42 (m, 1H), 4.04-4.15 (m, 4H), 3.98-3.99 (m, 1H), 3.80-3.90 (m, 1H), 3.57-3.63 (m, 1H), 1.67-1.80 (m, 2H), 1.69 (d, J=7.6 Hz, 6H), 1.51 (d, J=21.6 Hz, 3H), 1.41 (d, J=6.8 Hz, 6H), 1.37 (d, J=6.8 Hz, 3H), 0.57-0.69 (m, 2H)

The result of this physical and chemical analysis supports the chemical structure of the chemical formula (16).

(3.3) A glass plate of 1.8 cm square having a thickness of 0.12 to 0.17 mm was immersed in 10 ml of concentrated sulfuric acid, subjected to a sonication treatment for 15 minutes, washed with water and then immersed in 7 ml of concentrated sulfuric acid, 3 ml of 30% aqueous hydrogen peroxide was added dropwise thereto, and the glass plate was left for 12 hours, washed with water and dried at 150° C. for 5 hours to prepare a surface-activated glass plate.

(3.4) 2 g of THF and 500 µl of 2 N diluted hydrochloric acid were added to the allylsilane compound (16) (100 mg, 0.220 mmol), and the mixture was stirred at 60° C. for 17 hours to give a mixed composition containing a silane coupling agent having a free hydroxyl group and a silanol group that were derived from a polyol derivative that is the sugar derivative (15) and generated from the protective groups thereof by a deprotection reaction. Thereafter when the mixed composition was spin-coated at 1,500 rpm by using a spin coater on one surface of the surface-activated glass plate for forming a functional material, the triallylsilyl group of the allylsilane compound of the silane coupling agent that was derived from the allylsilane compound (16) and the protective group thereof formed a free hydroxyl group by a deprotection reaction, was subjected to a silane coupling reaction by a sol-gel process with the hydroxyl group exposed on the surface of the surface-activated glass plate, thereby propene was cleaved to give a plate-like functional material having free hydroxyl groups exposed thereon derived from the polyol derivative, which is a saccharide, to which the present invention is applied.

(3.5) The result of the physical and chemical analysis for the evaluation of the physical property using this as a defogging material is shown below. First, water was put into a test tube and heated in a hot water bath to thereby boil the water in the test tube, and the obtained plate-like functional material was placed on the opening of the test tube. When a defogging property test, which includes observing the sites of the functional material covering the inner space of the test tube until after 3 minutes have passed, was conducted, the functional material caused no fogging and thus showed a defogging property.

Example 4

(4.1) 2 g of THF and 250 µl of 2 N diluted sulfuric acid were added to an allylsilane compound (16) (100 mg, 0.220 mmol), which was prepared in a manner similar to Example 3, and the mixture was stirred at 60° C. for 5 hours to form a free hydroxyl group that derived from a polyol derivative, which is a saccharide, by a deprotection reaction of the protective group thereof. Thereafter 50 mol % of tetraethoxysilane (TEOS), which is one of tetraalkoxysilanes, was added and reacted at 60° C. for 12 hours, 26.7 µl of concentrated sulfuric acid was then added and reacted at 60° C. for 2 hours to effect functional group conversion, to thereby prepare a mixed composition containing a silane coupling agent that derived from the polyol derivative, which is a saccharide, and had a free hydroxyl group and a silanol group that were generated from the protective groups thereof by a deprotection reaction. When the mixed composition was spin-coated at 1,500 rpm by using a spin coater on one surface of the surface-activated glass plate prepared as in Example 3 for forming a functional material, the silanol group and partially-remained allyl group of the silane coupling agent that derived from the allylsilane compound (16) and in which a free hydroxyl group and a silanol group generated by a deprotection reaction of the protective groups thereof were subjected to a silane coupling reaction by condensation or polycondensation with the hydroxyl groups exposed on the surface of the surface-activated glass plate, thereby propene was cleaved to give a plate-like functional material to which the present invention is applied, having free hydroxyl groups derived from the polyol derivative, which is a saccharide.

(4.2) When contact angles were measured on an untreated glass plate and this functional material obtained by the treatment, the contact angle was 53° for the untreated, whereas the contact angle was 5° for the functional material obtained by the treatment.

(4.3) The result of the physical and chemical analysis for the evaluation of the physical property in a similar manner to Example 3 (3.5) using the obtained functional material as a defogging material is shown below. When a defogging property test, which includes observing the sites of the functional material covering the inner space of the test tube until after 3 minutes have passed, was conducted, the functional material caused no fogging and thus showed a defogging property. When the obtained defogging material was further washed with water and subjected to a defogging property test similarly, the defogging property was not affected.

Comparative Example 1

On the other hand, for comparison, a defogging property test was conducted in a similar manner to Example 3 (3.5) on a glass plate, which is an untreated cover glass, fogging was generated at after only 10 seconds had passed, and thus the glass plate did not show a defogging property.

Examples 5 to 7

A plate-like functional material to which the present invention is applied was obtained in a similar manner to Example 4, except that the tetraethoxysilane (TEOS) in Example 4 was changed to 10 mmol %, 25 mmol % and 100 mmol %, respectively. When these were subjected to a similar physical and chemical analysis to that in Example 4, similar results to that of Example 4 were shown.

Example 8

(8.1) 1 equivalent amount of oxalyl dichloride, 2 equivalent amount of triethylamine, 1 ml of anhydrous toluene and 0.5 ml of anhydrous dichloroethane were added to an allylsilane compound (16) (100 mg, 0.220 mmol) prepared as in Example 3, and the mixture was stirred at 40° C. for 5 hours and filtered with celite to thereby prepare a mixed composition, which was a filtrate containing a silane coupling agent in which the polyol derivative thereof, which is a saccharide, had been esterified and/or oligomerized. When the mixed composition was tip-coated on one surface of a surface-activated glass plate prepared as in Example 3 and heated at 100° C. for 2 days for forming a functional material, the allyl group derived from the allylsilane compound (16) of the silane coupling agent was subjected to a silane coupling reaction with the hydroxyl group exposed on the surface of the surface-activated glass plate, thereby propene was cleaved to give a plate-like functional material precursor having a polyol derivative. When the precursor was immersed in a mixed liquid of acetic acid-water (7:3 by a volume ratio), the protective group of the saccharide was deprotected to give a plate-like functional material to which the present invention is applied, having exposed free hydroxyl groups derived from the polyol derivative, as a defogging material.

(8.2) The result of the physical and chemical analysis for the evaluation of the physical property using this as a defogging material is shown below. When a defogging property test, which includes fogging the obtained plate-like functional material with breath and observing the site, was conducted, the functional material generated no fogging and thus showed a defogging property. Meanwhile, when an untreated glass plate was fogged with breath and the site was observed, fogging was generated and no defogging property was shown.

Example 9

(9.1) A plate-like functional material was obtained in a similar manner to Example 8, except that the heating was conducted at 100° C. for 1 day instead of heating at 100° C. for 2 days in the tip coating of Example 8.

(9.2) When a defogging property test was conducted in a similar manner to Example 8 using this as a defogging material, a defogging property was shown in a similar manner to Example 8.

Example 10

(10.1) An allylsilane compound (18) was obtained from 4-{3-(triallylsilyl)propyl}benzyl bromide (6) prepared in a similar manner to Example 1 and α-cyclodextrin (17), as shown in the following chemical reaction formula.

[Chemical Formula 15]

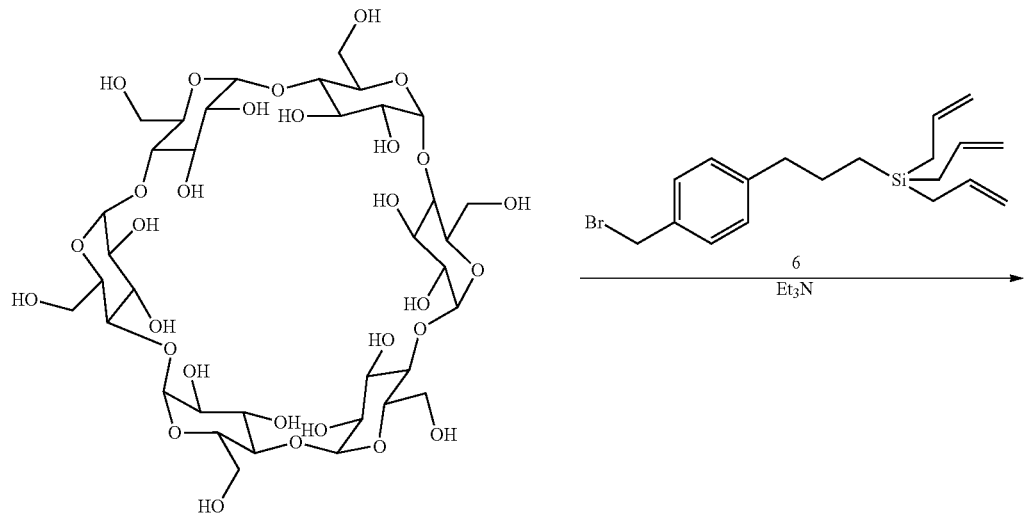

17

-continued

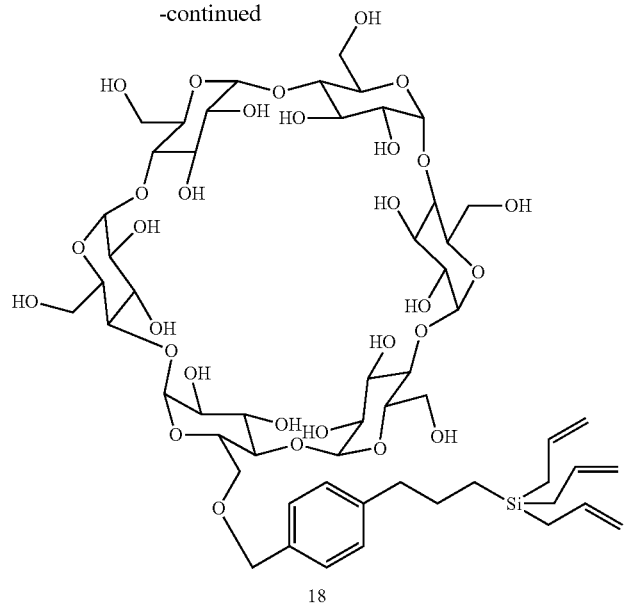

18

The result of this physical and chemical analysis by $^1$H NMR supports the chemical structure of the chemical formula (18).

(10.2) The allylsilane compound of the chemical formula (18) is used as a functional material, after being formed into a defogging material, by attaching the compound to a glass, or after being formed into a column chromatography support by which asymmetry can be identified, by attaching the compound to a substrate for a chromatography support such as a silica gel and a resin powder.

Example 11

(11.1) 60 mg of a cellulose powder (manufactured by MP Biomedicals, LLC, Item No. 191499) and 600 mg of lithium chloride were added to 7 mL of dimethylsulfoxide (DMSO) and stirred at 90° C. for 24 hours. Thereafter a solution containing 120 mg of a powder containing 60% of sodium hydride dissolved in 3 mL of DMSO was added thereto, the mixture was stirred at 60° C. for 1 hour, 891 mg of 3-bromopropyltriallylsilane (13) was added thereto, and the mixture was continuously stirred at 70° C. for 16 hours. Thereafter water was added thereto, and the mixture was filtered, washed with an aqueous solution of sodium thiosulfate, water, methanol and petroleum ether, and dried to give a yellow powder.

[Chemical Formula 16]

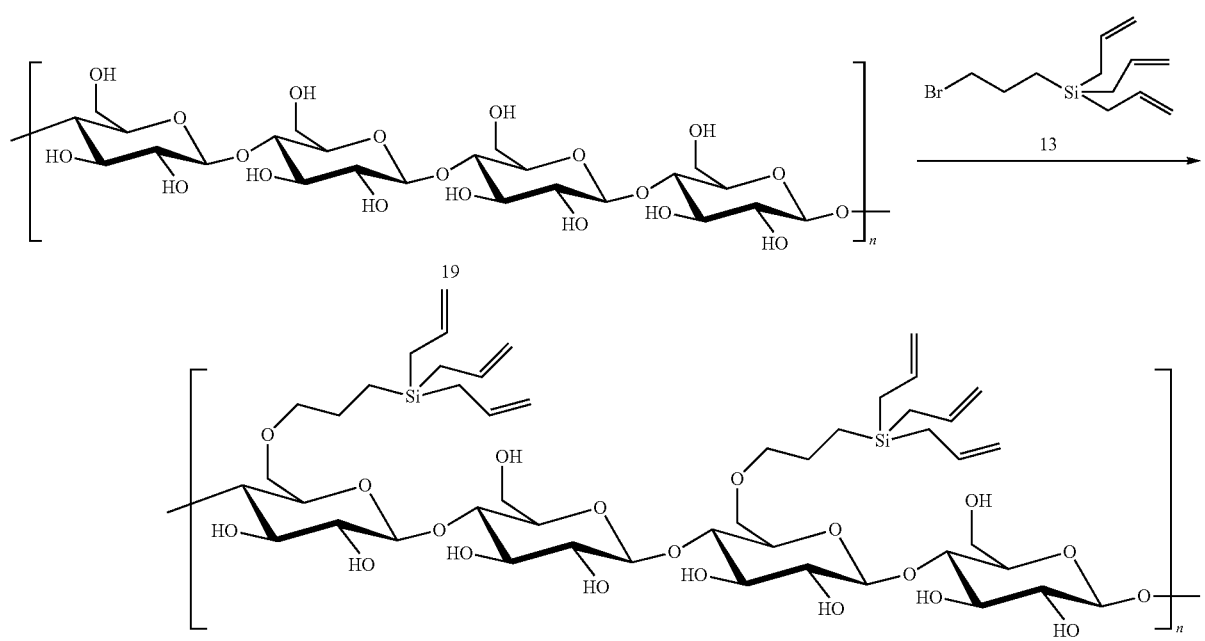

When a physical and chemical analysis of this by NMR was conducted, the result of this physical and chemical analysis supports the chemical structure of the chemical formula (20).

(11.2) Such allylsilane compound of the chemical formula (20) is used as a functional material, after being formed into a defogging material by attaching the compound to a glass, or after being formed into a column chromatography support by which asymmetry can be identified, by attaching the compound to a substrate for a chromatography support such as a silica gel and a resin powder.

Example 12

(12.1) Under a nitrogen atmosphere, NaH (45.3 mg, 1.11 mmol) was washed three times with hexane, tetrabutylammonium iodide (34.2 mg, 10 mol %) and benzyl alcohol (21) (100 µl, 0.93 mmol) dissolved in 2 ml of THF were added thereto, the mixture was stirred for 30 minutes, thereafter 4-{3-(triallylsilyl)propyl}benzyl bromide (6) (388 mg, 1.11 mmol) was added thereto, and the mixture was stirred for 13 hours. Thereafter methanol was added thereto, and the mixture was stirred for 30 minutes and slowly poured to ice/diethyl ether. The reaction mixture was neutralized by adding 1N diluted hydrochloric acid, and an aqueous solution of saturated sodium hydrogen carbonate was added. The aqueous layer was extracted with diethyl ether, and the combined organic layer was washed with saturated brine, dried over anhydrous sodium sulfate, filtered, and concentrated under a reduced pressure to give a crude product. The crude product was purified by separating by preparative layer chromatography (PLC) (developing solvent: n-hexane/ethyl acetate=20/1) to give an allylsilane compound (22) (yield amount: 151.8 mg, yield: 42%) to which the present invention is applied, as shown in the following chemical reaction formula.

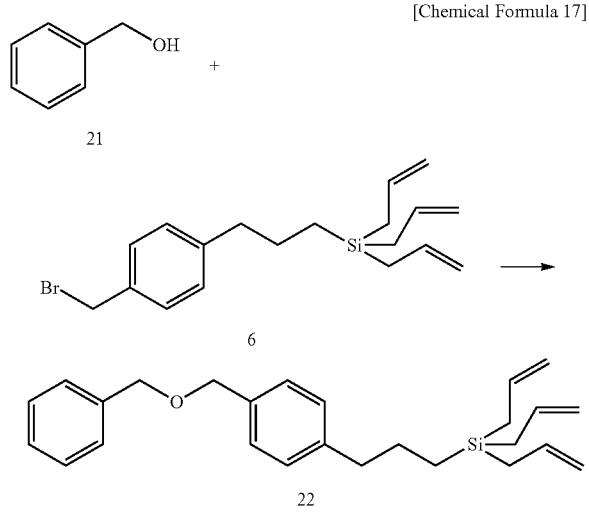

[Chemical Formula 17]

The result of the physical and chemical analysis of this by $^1$H NMR is shown below.

$^1$H NMR (CDCl$_3$) δ=7.29 (d, J=7.6 Hz, 2H), 7.16 (d, J=8.0 Hz, 2H), 7.07-7.12 (m, 5H), 5.73-5.80 (m, 3H), 4.84-4.89 (m, 6H), 4.67 (s, 2H), 4.50 (s, 2H), 2.56-2.63 (m, 2H), 1.60-1.68 (m, 2H), 1.58 (d, J=7.6 Hz, 6H), 0.62-0.66 (m, 2H)

The result of this physical and chemical analysis supports the chemical structure of the chemical formula (22).

(12.2) Such allylsilane compound of the chemical formula (22) is used as a functional material, after being formed into a defogging material, by attaching the compound to a glass, or after being formed into a column chromatography support, by attaching the compound to a substrate for a chromatography support such as a silica gel and a resin powder.

Example 13

(13.1) Under a nitrogen atmosphere, NaH (40.75 mg, 1.00 mmol) was washed three times with hexane, tetrabutylammonium iodide (30.7 mg, 10 mol %) dissolved in 2 ml of THF and isopropanol (23) (64.0 µl, 0.83 mmol) were added thereto, the mixture was stirred for 30 minutes, thereafter 4-{3-(triallylsilyl)propyl}benzyl bromide (6) (388 mg, 1.11 nimbi) was added thereto, and the mixture was stirred for 13 hours. Thereafter methanol was added thereto, and the mixture was stirred for 30 minutes and slowly poured to ice/diethyl ether. The reaction mixture was neutralized by adding 1N diluted hydrochloric acid, and saturated sodium hydrogen carbonate was added. The aqueous layer was extracted with diethyl ether, and the combined organic layer was washed with saturated brine, dried over anhydrous sodium sulfate, filtered, and concentrated under a reduced pressure to give a crude product. The crude product was purified by separating by preparative layer chromatography (PLC) (developing solvent: n-hexane/ethyl acetate=20/1) to give an allylsilane compound (24) (yield amount: 51 mg, yield: 18%) to which the present invention is applied, as shown in the following chemical reaction formula.

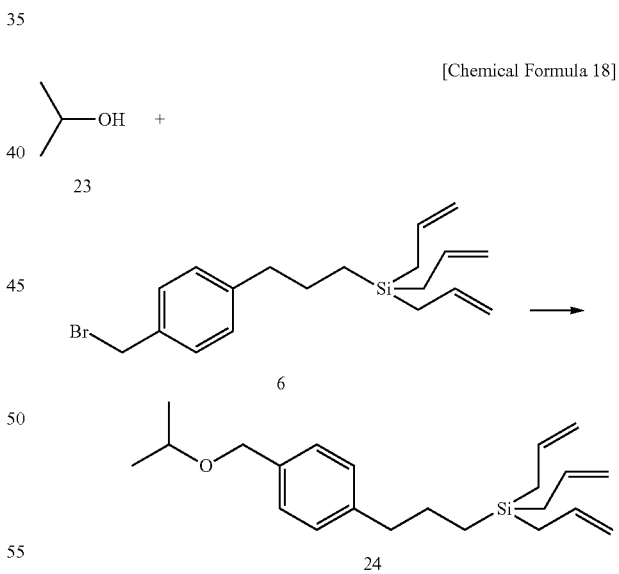

[Chemical Formula 18]

The result of the physical and chemical analysis of this by $^1$H NMR is shown below.

$^1$H NMR (CDCl$_3$) δ=7.29 (d, J=7.6 Hz, 2H), 7.16 (d, J=8.0 Hz, 2H), 5.73-5.80 (m, 3H), 4.84-4.89 (m, 6H), 4.48 (s, 2H), 3.65-3.70 (m, 1H), 2.57-2.63 (m, 2H), 1.60-1.68 (m, 2H), 1.57 (d, J=7.6 Hz, 6H), 1.21 (d, J=6.4 Hz, 6H), 0.61-0.67 (m, 2H)

The result of this physical and chemical analysis supports the chemical structure of the chemical formula (24).

(13.2) Such allylsilane compound of the chemical formula (24) is used as a functional material, after being formed into a defogging material by attaching the compound to a glass, or after being formed into a column chromatography support by attaching the compound to a substrate for a chromatography support such as a silica gel and a resin powder.

INDUSTRIAL APPLICABILITY

The (meth)allylsilane compound and the silane coupling agent having the compound according to the present invention express functionalities such as a defogging property and separation characteristics for column chromatography, and thus are useful as raw materials for functional materials such as a defogging material and a support for column chromatography.

This functional material is used as a defogging material for housewares and electronic and electric apparatuses for which prevention of fogging is required such as glass windows, eyeglasses and displays, and as a support for column chromatography for analysis and isolation in the field of fine chemicals and biochemicals.

According to the process for producing a functional material, this functional material can be simply produced at a fine yield rate with a high quality, and this the process is useful for the industrial production of the functional material.

What is claimed is:

1. A (meth)allylsilane compound comprising:
  a (meth)allylsilyl group-containing alkyl group or a (meth)allylsilylalkyl group-containing aralkyl group, which optionally has substituents and is bonded to a polyol comprising polysaccharides at the alkyl group of the (meth)allylsilyl group-containing alkyl group or at an alkylene group of the aralkyl group of the (meth)allylsilylalkyl group-containing aralkyl group.

2. The (meth)allylsilane compound according to claim 1,
  wherein the polyol has polyhydric free hydroxyl groups or at least one free hydroxyl group with partially-protected polyhydric hydroxyl groups in polyhydric hydroxyl groups.

3. The (meth)allylsilane compound according to claim 1, wherein the polysaccharides are selected from oligosaccharides, starches, celluloses, glycogens, and cyclodextrins.

4. The (meth)allylsilane compound according to claim 3, wherein the oligosaccharides are any of sucroses and maltoses, the starches are amyloses and/or amylopectins, the celluloses are any of cellulose, regenerated celluloses, cellulose ethers and cellulose esters, the glycogens are glycogen, and the cyclodextrins are any of $\alpha$-cyclodextrins, $\beta$-cyclodextrins and $\gamma$-cyclodextrins.

* * * * *